United States Patent [19]

Coates

[11] 4,403,037

[45] Sep. 6, 1983

[54] ERYTHROCYTE PREPARATIONS AND USE THEREOF IN HEMAGGLUTINATION TESTS

[75] Inventor: Stephen R. Coates, Leucadia, Calif.

[73] Assignee: American Hoechst Corporation, Somerville, N.J.

[21] Appl. No.: 195,864

[22] Filed: Oct. 10, 1980

[51] Int. Cl.$^3$ .................... C12Q 1/00; C12Q 1/70; G01N 33/48; G01N 33/54

[52] U.S. Cl. .................... 436/521; 424/3; 424/11; 424/86; 424/89; 435/5; 435/7; 435/29; 436/520; 436/547

[58] Field of Search .................... 424/2, 3, 8, 11, 12, 424/13, 86, 89; 435/4, 5, 7, 29, 235, 238; 23/230 B; 436/520, 521, 547

[56] References Cited

U.S. PATENT DOCUMENTS

| | | | |
|---|---|---|---|
| 3,714,345 | 1/1973 | Hirata | 424/3 |
| 4,004,979 | 1/1977 | Avrameas | 435/7 X |
| 4,176,174 | 11/1979 | Russell | 424/86 |
| 4,195,074 | 3/1980 | Safford | 424/12 |

FOREIGN PATENT DOCUMENTS

| | | | |
|---|---|---|---|
| 1244344 | 8/1971 | United Kingdom . | |
| 1257263 | 12/1971 | United Kingdom | 424/12 |
| 1284947 | 8/1972 | United Kingdom . | |
| 1286857 | 8/1972 | United Kingdom . | |
| 1442546 | 7/1976 | United Kingdom . | |

OTHER PUBLICATIONS

Kennedy, Clin. Chim Acta, vol. 70, 1976, pp. 1–7, 17–25.
Levy, J. Immunol. Methods, vol. 22, 1978, pp. 131–142.

*Primary Examiner*—Anna P. Fagelson
*Attorney, Agent, or Firm*—Natalie Jensen

[57] ABSTRACT

Erythrocytes are coated with specific hemagglutinating virus antigen and then treated to produce a stabilized, antigen coated erythrocyte preparation which is used in the determination of antibody in biological fluids.

15 Claims, No Drawings

ERYTHROCYTE PREPARATIONS AND USE THEREOF IN HEMAGGLUTINATION TESTS

BACKGROUND OF THE INVENTION

A widely used procedure for the determination of antibody to rubella virus in human serum is the hemagglutination inhibition test (HAI). The approved standard rubella hemagglutination inhibition test is described in APPROVED STANDARD: ASM-5, National Committee for Clinical Laboratory Standards, Villanova, Pa. 19085 (1979). The test is based on the principle that agglutination of chick erythrocytes by rubella antigen can be inhibited by antibodies specific for the antigen. A commercially available HAI test is the Rubesure® Test (Calbiochem-Behring Corp., La Jolla, Calif.) which operates on the same principle but utilizes human erythrocytes. Antibody titers measured by the Rubesure® test are approximately 2-fold greater than titers measured by the standard HAI test, the difference being due to the species of erythrocyte employed. Although HAI tests are extremely reliable and exhibit excellent sensitivity, they are very time consuming, i.e., the tests require extensive pretreatment of the test sera and involve at least one fairly lengthy incubation so that in most laboratories such tests are performed over two days.

Another type of procedure for the determination of antibody to rubella virus in human serum is the indirect or passive hemagglutination test (PHA). A commercially available PHA test is the Rubacell® Diagnostic Test (Abbott Laboratories, Chicago, Ill.). The test is based on the agglutination of stabilized human erythrocytes coated with rubella virus soluble antigen in the presence of antibody to the rubella virus. While the Abbott PHA test exhibits comparable sensitivity to HAI tests, it is much less time consuming than HAI tests since it does not require pretreatment of test sera. Final test results with the Abbott test may be obtained approximately 2 hours after test fluid collection.

SUMMARY OF THE INVENTION

The present invention relates to methods and materials useful in the determination of virus antibodies in biological fluids.

Accordingly, a first aspect of the present invention relates to a method for producing a stabilized, antigen coated erythrocyte preparation, which method comprises:
- (a) providing a suspension of erythrocytes in buffered saline;
- (b) treating the erythrocyte suspension with specific hemagglutinating virus antigen to obtain erythrocytes having antigen coating the surface thereof;
- (c) treating the antigen coated erythrocytes with a cross-linking agent to obtain stabilized, antigen coated erythrocytes; and
- (d) treating the stabilized, antigen coated erythrocytes with a blocking agent to eliminate unreacted functional groups associated with treatment of the antigen coated erythrocytes with cross-linking agent.

Another aspect of the present invention relates to a method for producing a stabilized, antigen coated erythrocyte preparation, which method comprises subjecting the antigen coated erythrocytes of (b) above to at least one of the following:
- (1) treatment with an enzyme;
- (2) treatment with heat;
- (3) treatment with an acid; and
- (4) treatment with an alkylating agent;

prior to treatment with cross-linking agent (c) and subsequent treatment with blocking agent (d).

Still another aspect of the present invention relates to stabilized, antigen coated erythrocyte preparations obtained by any of the above described methods.

A further aspect of the present invention relates to a method for determining antibody to a hemagglutinating virus antigen in a biological fluid suspected of containing the antibody, which method comprises:
- (1) contacting a sample of the fluid with a buffered aqueous suspension of stabilized, antigen coated erythrocytes, prepared as previously described; and
- (2) incubating the mixture of sample and coated erythrocytes;

whereby the presence in the sample of antibody to hemagglutinating virus antigen results in agglutination of the antigen coated erythrocytes.

Finally, a particularly important aspect of the present invention relates to a stabilized, rubella antigen coated erythrocyte preparation and use of such a preparation in the determination of rubella antibody in biological fluids.

DETAILED DESCRIPTION

Antigenic substances utilized to prepare the antigen coated erythrocyte preparations of the instant invention include hemagglutinating viruses as well as hemagglutinating virus antigens contained in such viruses. Representative hemagglutinating viruses include, for example, rubella virus, influenza virus, parainfluenza virus, measles virus and the like.

Erythrocytes employed in the instant invention include mammalian erythrocytes, particularly human, and avian erythrocytes such as those from turkeys, chickens, geese, pigeons and the like. The erythrocytes are collected in whole blood treated with a conventional anticoagulant. The cells are packed by centrifugation and then washed with a buffered saline solution having a substantially neutral pH to prevent hemolysis and to remove protein material present in the serum.

A suspension of the washed erythrocytes in buffered saline is treated with hemagglutinating virus antigen to obtain erythrocytes having antigen coating the surface thereof. The volume of packed erythrocytes employed is minor relative to the total volume, i.e., the suspension preferably contains from about 0.1% to 0.4% by volume of erythrocytes. In general the erythrocytes are coated with antigen in buffered saline having a pH below 8, preferably from about 6 to 8. In addition to the two essential components, i.e., erythrocytes and antigen, various other components may be present during the coating step in order to adjust the physiological environment, as needed. For example, salts such as calcium chloride, magnesium chloride and manganese chloride may be incoporated if needed to facilitate attachment of the antigen to the erythrocytes. Such attachement is usually complete in about 4 hours, but certain antigens may require as long as 16 hours. The erythrocytes are preferably treated with antigen at room temperature (24° C.) since higher temperatures tend to reduce the sensitivity of the final preparation. After adequate coating is attained, the antigen coated erythrocytes are washed several times with buffered saline having a neutral pH to remove excess antigen.

The antigen coated erythrocytes are then resuspended in buffered saline and treated with a cross-linking agent. The suspension of coated erythrocytes is prepared in saline buffered to a pH of 5.5 to 9, preferably from about 6 to 7. The suspension preferably contains 0.1 to 0.4% by volume coated erythrocytes. Treatment with cross-linking agent is carried out at room temperature for a period of 30 minutes to 4 hours. The amount of cross-linking agent employed in the treatment ranges from about 0.02 to 0.2% (w/v) per total volume of coated erythrocyte suspension. Following treatment, the antigen coated erythrocytes are washed extensively with aqueous media having a neutral pH. Suitable cross-linking agents that may be employed in the treatment of antigen coated erythrocytes according to instant invention include, for example, dialdehydes such as glutaraldehyde, succinic dialdehyde and the like; bis-imidates such as dimethyl suberimidate, dimethylglutarimidate and the like; activated diolofins such as divinyl sulfone, N,N-bismethylene bisacrylamide and the like; diepoxides such as 1,4-butanediol diglycidyl ether, 1, 2, 3, 4 diepoxy butane and the like; aliphatic dihalides such as 1,4-dichlorobutane, 1,4-dibromobutane, 1,3-dichloropropane and the like; aromatic dihalides such as 2,4-dinitro-1,5-difluorobenzene and the like; and aliphatic diacyl halides such as adipoyl chloride and the like.

Treatment of the antigen coated erythrocytes with a cross-linking agent serves a dual purpose, i.e., the treatment serves to stabilize the coated erythrocytes and reduces the hemagglutinating activity of same. Stabilization, which is effected by reaction of the cross-linking agent with free amino groups on the surface of the coated erythrocytes, produces a semi-rigid structure which exhibits enhanced stability during subsequent use of the preparation in the determination of virus antibody. Reduction of hemagglutinating activity, which is effected by reaction of the cross-linking agent with (1) receptor sites on the erythrocytes and (2) hemagglutinating moieties on the antigen, prevents the antigen coated erythrocytes from undergoing spontaneous agglutination in the absence of antibody specific to the hemagglutinating antigen.

In certain instances it may be desirable to subject the antigen coated erythrocytes to additional treatment prior to treatment with a cross-linking agent. Such additional treatment comprises subjecting the coated erythrocytes to at least one of the following:
(1) treatment with an enzyme;
(2) treatment with heat;
(3) treatment with acid; and
(4) treatment with an alkylating agent.

The purpose of the foregoing treatment(s) is to reduce the hemagglutinating activity of the coated erythrocytes prior to treatment with a cross-linking agent so that the later operation can proceed without interference from spontaneous agglutination.

The necessity of reducing the level of hemagglutinating activity prior to cross-linking depends on the species of antigen used in the coating, the purity of the antigen and the species of erythrocyte employed. The practitioner of the instant invention can readily determine the necessity of reducing the hemagglutinating activity prior to cross-linking by reference to the occurrence of spontaneous agglutination of a cross-linked antigen coated erythrocyte preparation in the absence of specific antibody.

When treatment with an enzyme is utilized to reduce hemagglutinating activity, such treatment is carried out by contacting a suspension of antigen coated erythrocytes with a suitable enzyme. The suspension of coated erythrocytes is prepared in saline solution buffered at the pH optimum of the enzyme and containing any ions required for enzymatic activity. Preferably, the suspension contains 0.1 to 0.4% by volume coated erythrocytes. The enzymatic treatment is carried out at the optimum temperature for the enzyme for a period of time sufficient to reduce the hemagglutinating activity, i.e., from about 30 minutes to 2 hours. The amount of enzyme employed in the treatment of antigen coated erythrocytes ranges from about 0.0001 to 1 International Units per volume of coated erythrocyte suspension. Advantageously, the enzyme is employed in the form of a solution in aqueous solvent. Following enzymatic treatment, the antigen coated erythrocytes are washed several times with saline solution having a neutral pH to remove residual enzyme. Suitable enzymes that may be utilized to reduce the hemagglutinating activity include, for example, proteolylic enzymes such as trypsin, chymotrypsin, pepsin and the like and glycolytic enzymes such as $\beta$-galactosidase, $\beta$-glucosidase and the like.

When treatment with heat is utilized to reduce the hemagglutinating activity, such treatment is carried out by maintaining a suspension of antigen coated erythrocytes at a temperature from about 37° to 45° C. for a period of time sufficient to reduce the hemagglutinating activity, i.e., from about 30 minutes to 16 hours. The suspension of coated erythrocytes is prepared in buffered saline having a pH of 6 to 8. Preferably, the suspension contains 0.1 to 0.4% by volume coated erythrocytes.

When treatment with an acid is used to reduce hemagglutinating activity, such treatment is carried out by titrating a suspension of antigen coated erythrocytes to a pH of 3 to 5 with a suitable acid and thereafter incubating the titrated preparation at room temperature for a period of 30 minutes to 16 hours. The suspension of coated erythrocytes is prepared in saline solution having a neutral pH. Preferably, the suspension contains 0.1 to 0.4% by volume coated erythrocytes. Following acid treatment, the antigen coated erythrocytes are washed several times with saline solution having a neutral pH. Suitable acids that may be utilized to reduce the hemagglutinating activity include, for example, inorganic acids such as hydrochloric acid, sulfuric acid, hydrobromic acid and the like and organic acids such as p-toluene-sulfuric acid, trichloroacetic acid and the like.

When an alkylating agent is used to reduce hemagglutinating activity, such treatment is carried out by contacting a suspension of antigen coated erythrocytes with a suitable alkylating agent. The suspension of coated erythrocytes is prepared in buffered saline having of pH of 6 to 8. Preferably, the suspension contains 0.1 to 0.4% by volume coated erythrocytes. The alkylating treatment is carried out at room temperature for a period of time sufficient to reduce the hemagglutinating activity, i.e., from about 1 to 16 hours. The amount of alkylating agent employed in the treatment of antigen coated erythrocytes ranges from about 0.1 to 10 mg. per volume of coated erythrocyte suspension. Advantageously, the alkylating agent is employed in the form of a solution in aqueous solvent. Following treatment with alkylating agent, the antigen coated erythrocytes are washed several times with saline solution having a netural pH. Suitable alkylating agents that may be used to reduce the hemagglutinating activity include, for example, β-propiolactone, 1,3-propane sultone, dimethylsulfate, iodoacetic acid and the like.

Antigen coated erythrocytes which are treated to reduce hemagglutinating activity prior to cross-linking treatment are subsequently treated with a cross-linking agent as described above.

Following treatment with cross-linking agent, the stabilized, antigen coated erythrocytes are treated with a blocking agent to eliminate unreacted functional groups associated with treatment of the coated erythrocytes with cross-linking agent. The elimination of unreacted functional groups is accomplished by contacting a suspension of stabilized antigen coated erythrocytes with a suitable blocking agent at room temperature for a period of 6 to 16 hours. The suspension of stabilized, coated erythrocytes is prepared in aqueous media having a pH of 6 to 8. Preferably, the suspension contains 0.1 to 0.4% by volume stabilized, coated erythrocytes. The amount of blocking agent employed ranges from 10 to 1,000 millimoles per volume of stabilized, antigen coated erythrocyte suspension. Following treatment, the stabilized, coated erythrocytes are washed several times with aqueous media having a neutral pH to remove excess blocking agent. Suitable blocking agents that may be advantageously employed in the instant invention include, for example, primary aliphatic amines such as methylamine, ethanolamine, tris(hydroxymethyl)aminomethane and the like, secondary amines such as diethylamine, diethanolamine and the like, aliphatic thiols such as ethanethiol, 2-mercaptoethanol, 2-methyl-2-butanethiol and the like; and amino acids such as lysine, glycine, arginine and the like. Following treatment, the stabilized antigen coated erythrocytes are washed several times with aqueous media having a neutral pH.

The coated erythrocyte preparations of the instant invention may be stored in the lyophilized state or at a temperature of about 4° to −70° C. until utilized for hemagglutination testing. Improved results upon reconstitution are obtained if the coated erythrocytes are lyophilized in aqueous solution containing ethylenediaminetetraacetic acid. The quantity of stabilized, coated erythrocytes in the solution is not critical and may vary from about 0.1 to 1 percent of the total volume of the preparation. The stability of reconstituted coated erythrocytes, when stored at 2° to 8° C., is six months or greater.

The method for determining antibody to hemagglutinating virus antigen in a biological fluid suspected of containing the antibody comprises (1) contacting a sample of the fluid with a buffered aqueous suspension of stabilized, antigen coated erythrocytes provided as previously described and (2) incubating the mixture of sample and coated erythrocytes whereby the presence in the fluid sample of antibody to hemagglutinating virus antigen effects agglutination of the antigen coated erythrocytes.

Although hemagglutinating testing according to the instant invention may be performed using various techniques, a preferred technique is standard microtiter hemagglutinating testing which employs:

(1) a sample of biological fluid suspected of containing antibody to a hemagglutinating virus antigen;

(2) a suspension of stabilized, antigen coated erythrocytes in aqueous media having a pH of 6 to 8.

(3) a positive control (known to contain antibody); and (4) a negative control (free of antibody).

When qualitative test results are desired, approximately 50 μl of 1:10 dilutions of test fluid, positive control and negative control are added to separate wells in a microtiter plate and contacted with approximately 25 μl of a suspension of coated erythrocytes. The suspension contains $1 \times 10^6$ to $8 \times 10^7$ cells, preferably $1 \times 10^7$ to $3 \times 10^7$ cells per ml of suspension. The plate is shaken for 10 seconds and then incubated at room temperature for at least two hours. Following incubation, the test sample is compared visually with both positive and negative controls. The negative control will exhibit a compact button of coated erythrocytes at the bottom of the well, indicating nonagglutination, whereas the positive control will exhibit a diffuse pattern of coated erythrocytes spread over the bottom of the well, indicating agglutination. When the test sample exhibits a compact button similar in size to that of the negative control, the test is negative for antibody to hemagglutinating virus antigen. When the test sample exhibits a pattern where the button is more diffuse than the negative control, i.e., similar to the positive control, the test is positive for antibody.

When quantitative test results are desired, 50 μl of two-fold serial dilutions of test fluid and 50 μl of 1:10 dilutions of positive and negative controls are added to separate wells in a microtiter plate and contacted with 25 μl of a suspension of coated erythrocytes. The suspension contains $1 \times 10^6$ to $8 \times 10^7$ cells, preferably $1 \times 10^7$ to $3 \times 10^7$ cells per ml of suspension. The plate is shaken for 10 seconds and then incubated at room temperature for at least two hours. Following incubation, the serial dilutions of test fluid are visually compared with both positive and negative controls as described earlier. The reciprocal of the highest serial dilution exhibiting agglutination is the antibody titer.

When polystyrene microtiter plates are employed in hemagglutination testing, it is desirable that the diluent used for dilution of test sera contain from about 0.001 to 0.3% nonionic detergent. The incorporation of detergent reduces the tendency of the coated erythrocytes to bind non-specifically to the polystyrene. Suitable nonionic detergents that may be employed for this purpose include, for example, Tween 20 (polyoxyethylene sorbitan monolaurate), Tween 80 (polyoxyethylene sorbitan mono-oleate), Triton X-100 (polyethylene glycol p-isooctylphenyl ether) and the like.

The term "aqueous media" as used herein refers to water as well as physiological saline (a 0.9% solution of sodium chloride in water). Suitable buffers that may be used to adjust the pH of the aqueous media include, for example, tris-(hydroxymethyl)aminomethane, phosphate buffers, glycine and the like. The term "antigen" as used herein refers to intact hemagglutinating viruses as well as hemagglutinating virus antigens contained in such viruses.

Biological fluids which may be examined for the presence of specific antibodies to hemagglutinating virus antigens according to the instant invention include, for example, serum, plasma, cord blood and nasal secretions.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE I

Rubella hemagglutinating antigen is isolated from a culture medium of rubella virus infected cells according to the procedure described infra. The cell line employed to obtain the antigen is Baby Hamster Kidney (BHK-21), 13S clone (ATCC #CCL10). The virus used to infect the cells is Rubella, B127 strain (ATCC #VR553).

Cell monolayers from eight or nine 32 oz. prescription bottles are trypsinized and the cell collection pooled and diluted to a volume of 800 ml with Wistar Growth medium containing 10% inactivated, fetal calf serum. The cell count ranges from 0.5 to $1.0\times10^6$ cells per ml. Wistar Growth medium is composed of Eagle's Minimum Essential Media prepared in Hank's Basal Salt Solution with a double concentration of vitamins and amino acids (except 1X glutamine); 4.5 gm/liter glucose; 0.1 mg/liter ferric nitrate and 10% tryptose phosphate broth.

The resulting suspension culture is incubated with stirring at 35° C. for 24 hours. Thereafter, the suspension is decanted into sterile centrifuge bottles and spun at 500X g for 10 minutes. The supernatant fluid is then discarded and the packed cells are resuspended in 100 ml of Wistar Maintenance medium containing 0.4% bovine albumin fraction V. Fifteen ml of rubella seed virus is added to the suspension which is then incubated with stirring for 2 hours at 35° C. Thereafter, additional Wistar Maintenance medium is added to the suspension to bring the volume to 800 ml and the pH is adjusted to 7.3 to 7.4 by the addition of 7% sodium bicarbonate solution. The suspension is then incubated for 24 hours at 35° C.

Following incubation, the suspension is centrifuged at 500×g for 10 minutes. The supernatant fluid is discarded and the cells are resuspended in 800 ml of fresh Wistar Maintenance Medium preadjusted to pH 7.3 to 7.4. The suspension is then reincubated at 35° C. for approximately 5 to 8 days. During this period, the culture is monitored daily for hemagglutinin development. Peak hemagglutinating activity is generally observed on the 7th day after inoculation. When peak activity is observed, the culture is treated with Tween 80 (polyoxyethylene (20) sorbitan monooleate) and ether. The Tween 80/ether treatment comprises adding to the culture 0.125 ml of undiluted Tween 80 for each 100 ml of supernatant fluid. After addition, the culture is stirred at 4° C. for 15 minutes. Thereafter, a volume of ethyl ether equal to ½ the volume of supernatant fluid is added to the culture which is stirred at 4° C. for an additional 15 minutes. The treated culture is then centrifuged at 700×g for 20 minutes at 4° C. The aqueous layer is aspirated and bubbled with nitrogen to remove residual ether. Continuous gentle stirring accelerates evaporation. When all residual ether is removed, a hemagglutination test is performed to determine the titer of the final product.

The hemagglutinating titer of rubella antigen prepared according to the above procedure is between 32 to 256 HA units per 0.025 ml.

EXAMPLE II

Human type O erythrocytes obtained from whole anticoagulated blood are washed three times with 0.05 M phosphate buffered saline, pH 7.4. The washed erythrocytes are then resuspended in buffered saline to provide a 0.4% v/v erythrocyte suspension. Hemagglutinating rubella virus antigen, obtained by the process recited in EXAMPLE I, is added to the 0.4% suspension to provide a final concentration of 16 hemagglutinating units of antigen per ml of suspension. The suspension is then incubated for 3 hours at room temperature. During incubation, the suspension is repeatedly dispersed by pipetting to prevent agglutination. Following incubation, the antigen coated erythrocytes are washed with buffered saline to remove any unadsorbed antigen.

EXAMPLE III

Antigen coated erythrocytes, prepared according to the method recited in EXAMPLE II, are suspended in phosphate buffered saline, pH 7.4, to provide a 0.4% by volume concentration. Glutaraldehyde is added to the 0.4% suspension to provide a final concentration of 0.1% (v/v) aldehyde per total volume of suspension. The suspension is maintained at room temperature for approximately 60 minutes. Thereafter, the stabilized, antigen coated erythrocytes are washed repeatedly with buffered saline.

A 0.4% v/v suspension of the stabilized, coated erythrocytes prepared in phosphate buffered saline, pH 7.4, is treated with sufficient tris-(hydroxymethyl-)aminomethane (TRIS) to provide a final TRIS concentration of 0.5 M. The suspension is maintained at room temperature for 15 hours. Thereafter the stabilized, antigen coated erythrocytes are washed several times with buffered saline and then resuspended in buffered saline to provide a suspension containing 0.1 to 0.4% by volume stabilized antigen coated erythrocytes.

EXAMPLE IV

Antigen coated erythrocytes, prepared according to the method recited in EXAMPLE II, are suspended in carbonate buffered saline, pH 8.5, to provide a 0.4% by volume concentration. The suspension is treated with sufficient 2,4-dinitro-1,5-difluorobenzene to provide a concentration of 75 μM. The suspension is then maintained at room temperature for approximately 12 hours. Thereafter, the stabilized, antigen coated erythrocytes are washed repeatedly with carbonate buffered saline.

A 0.4% v/v suspension of the stabilized, coated erythrocytes, prepared in carbonate buffered saline, pH 8.5, is treated with sufficient lysine to provide a lysine concentration of 0.05 M. The suspension is maintained at room temperature for approximately 12 hours. Thereafter, the stabilized, antigen coated erythrocytes are washed several times with neutral buffered saline and then resuspended in buffered saline to provide a suspension containing 0.1 to 0.4% by volume stabilized, antigen coated erythrocytes.

EXAMPLE V

Antigen coated erythrocytes, prepared according to the method recited in EXAMPLE II are suspended in a 0.4% by volume concentration in TRIS buffered saline, pH 8.5 containing 0.02 M calcium chloride. Dimethylsuberimidate is added to the 0.4% suspension to provide a final concentration of 10 μg/ml of suspension. The suspension is maintained at room temperature for 6 hours. Thereafter, the stabilized antigen coated erythrocytes are washed repeatedly with tris suffered saline.

A 0.4% v/v suspension of the stabilized coated erythrocytes, prepared in buffered saline, pH 7, is treated with sufficient lysine to provide concentration of 0.1 M. The suspension is maintained at room temperature for approximately 24 hours. Thereafter, the stabilized, antigen coated erythrocytes are washed several times with neutral buffered saline and then resuspended in buffered saline to provide a suspension containing 0.4% by volume stabilized antigen coated erythrocytes.

EXAMPLE VI

Stabilized, rubella antigen coated erythrocytes, prepared according to the method of EXAMPLE III, are suspended in 0.05 M tris buffer, pH 7.2, to provide a concentration of $1 \times 10^6$ cells per ml of suspension. The diluent used for dilution of test sera is 0.05 M tris buffered saline containing 0.2% (w/v) Tween 20 (polyoxyethylene sorbitan monolaurate). For qualitative testing, 1:10 dilutions of test sera (including positive and negative controls) are prepared in the diluent. For quantitative testing, serial two-fold dilutions of test sera and 1:10 dilutions of positive and negative controls are prepared in the diluent.

Fifty μl of diluted serum and 50 μl of diluted positive and negative controls are added to separate wells in a plastic microtiter plate. Twenty-five μl of stabilized, rubella antigen coated erythrocyte suspension is then added to each well. The plate is shaken for 10 seconds and incubated at room temperature for at least 2 hours.

In qualitative testing, the test serum is compared visually with both positive and negative controls. For quantitative testing, the highest serial dilution exhibiting agglutination is selected as the rubella antibody titer.

EXAMPLE VII

Typical results achieved utilizing the test procedure of the instant invention are compared with prior art procedures in the following tables.

TABLE I

Comparative results with 100 serum specimens tested qualitatively for the presence of rubella antibody titers greater than 10.

| Qualitative Results | #1 | #2 |
|---|---|---|
| Positive | 88 | 88 |
| Negative | 12 | 12 |

1 Antibodies detected per EXAMPLE VI.
2 Antibodies detected using the commercially available Rubesure® Test (Calbiochem-Behring Corp.).

TABLE II

Comparative results with 41 serum specimens tested quantitatively for rubella antibody levels:

| | Rubella Antibody Titer | |
|---|---|---|
| Sample No. | #1 | #2 |
| 1 | <8 | <8 |
| 2 | <8 | <8 |
| 3 | <8 | <8 |
| 4 | 256 | 512 |
| 5 | <8 | <8 |
| 6 | 256 | 512 |
| 7 | 32 | 32 |
| 8 | 32 | 64 |
| 9 | 32 | 32 |
| 10 | 32 | 64 |
| 11 | 128 | 128 |
| 12 | 128 | 256 |
| 13 | 64 | 64 |
| 14 | 64 | 128 |
| 15 | 32 | 32 |
| 16 | 64 | 32 |
| 17 | 64 | 128 |
| 18 | 64 | 64 |
| 19 | 128 | 128 |
| 20 | 64 | 32 |
| 21 | <8 | <8 |
| 22 | 64 | 32 |
| 23 | 32 | 32 |
| 24 | 16 | 16 |
| 25 | 32 | 32 |
| 26 | 64 | 64 |
| 27 | 64 | 64 |
| 28 | 16 | 16 |
| 29 | 64 | 64 |
| 30 | 64 | 128 |
| 31 | 8 | 8 |
| 32 | 64 | 32 |
| 33 | 64 | 128 |
| 34 | 64 | 64 |
| 35 | 32 | 32 |
| 36 | 256 | 256 |
| 37 | 256 | 256 |
| 38 | <8 | <8 |
| 39 | <8 | <8 |
| 40 | 128 | 128 |
| 41 | 32 | 32 |

1 Antibody titers determined per EXAMPLE VI.
2 Antibody titers determined using the commercially available Rubesure® Test (Calbiochem-Behring Corp.)
The regression equation for the above comparison is Y = 1.03X − 1.06 (where Y = #1 and X = #2); the coefficient of correlation (r) is 0.90.

TABLE III

Comparative results with 40 acute and convalescent paired serum specimens tested quantitatively for rubella antibody levels.

| | Rubella Antibody Titer | | |
|---|---|---|---|
| Sample No. | #1 | #2 | #3 |
| 1 acute | <8 | <8 | <8 |
| 1 convalescent | 64 | <8 | 128 |
| 2 acute | <8 | <8 | <8 |
| 2 convalescent | 32 | <8 | 64 |
| 3 acute | <8 | <8 | <8 |
| 3 convalescent | 64 | <8 | 128 |
| 4 acute | <8 | <8 | <8 |
| 4 convalescent | 16 | <8 | 64 |
| 5 acute | <8 | <8 | <8 |
| 5 convalescent | 64 | <8 | 256 |
| 6 acute | <8 | <8 | <8 |
| 6 convalescent | 256 | 512 | 512 |
| 7 acute | <8 | <8 | <8 |
| 7 convalescent | 32 | <8 | 128 |
| 8 acute | <8 | <8 | <8 |
| 8 convalescent | 64 | <8 | 256 |
| 9 acute | 16 | <8 | 16 |
| 9 convalescent | 64 | 16 | 256 |
| 10 acute | 8 | 8 | 32 |
| 10 convalescent | 64 | 16 | 512 |

1 Antibody titers determined per Example VI.
2 Antibody titers determined using the commercially available Rubacell® Diagnostic Test (Abbott Laboratories, Chicago, Illinois).
3 Antibody titers determined using the commercially available Rubesure® Test (Calbiochem-Behring Corp.)

It is apparent from the results summarized in the above tables that the test procedure of the instant invention, employing stabilized, coated erythrocytes produced according to the instant invention provides a rapid, sensitive and specific method for determining rubella specific antibody. Further, it is apparent that use of the stabilized, coated erythrocytes, as described herein, provides a means for determining rubella specific antibody in patients with recent rubella infections.

What is claimed is:

1. A method of producing a stabilized, antigen coated erythrocyte preparation, which method comprises:
   (a) providing a suspension of erythrocytes in buffered saline;
   (b) treating said erythrocyte suspension with a specific hemagglutinating virus antigen to obtain erythrocytes having antigen coating the surface thereof;
   (c) stabilizing said antigen coated erythrocyte suspension by treating said antigen coated erythrocyte suspension with a cross-linking agent for a period of time sufficient to reduce the hemagglutinating activity of said antigen coated erythrocyte suspension to prevent spontaneous agglutination thereof; and
   (d) treating said stabilized, antigen coated erythrocyte suspension with a blocking agent to eliminate unreacted functional groups associated with treatment of said antigen coated erythrocytes with a cross-linking agent.

2. A method according to claim 1 wherein said cross-linking agent is selected from the group consisting of dialdehydes, bisimidates, activated diolefins, diepoxides, aliphatic dihalides, aromatic dihalides and aliphatic diacylhalides.

3. A method according to claim 1 wherein said blocking agent is selected from the group consisting of primary aliphatic amines, secondary aliphatic amines, aliphatic thiols and amino acids.

4. A method according to claim 1 wherein said antigen is rubella hemagglutinating antigen.

5. A method according to claim 4 wherein said dialdehyde is glutaraldehyde.

6. A method according to claim 5 wherein said blocking agent is tris-(hydroxymethyl)aminomethane.

7. The method as defined in claim 1 wherein said treating is carried out at room temperature for a period of time ranging from 30 minutes to 4 hours and wherein said cross-linking agent ranges in concentration from 0.02 to 0.2% by weight per volume of antigen coated erythrocyte suspension containing 0.1 to 0.4% by volume of antigen coated erythrocytes.

8. A stabilized antigen coated erythrocyte preparation obtained by the method of claim 1, 2, 3, 4, 5 or 6.

9. A method for determining antibody to a hemagglutinating virus antigen in a biological fluid suspected of containing said antibody, which comprises:
   (i) contacting a sample of said fluid with a buffered aqueous suspension of stabilized, antigen coated erythrocytes wherein said erythrocytes have been prepared by:
      (a) providing a suspension of erythrocytes in buffered saline;
      (b) treating said erythrocyte suspension with a specific hemagglutinating virus antigen to obtain erythrocytes having antigen coating the surface thereof;
      (c) stabilizing said antigen coated erythrocyte suspension by treating said antigen coated erythrocyte suspension with a cross linking agent for a period of time sufficient to reduce the hemagglutinating activity of said antigen coated erythrocyte suspension to prevent spontaneous agglutination thereof; and
      (d) treating said stabilized, antigen coated erythrocyte suspension with a blocking agent to eliminate unreacted functional groups associated with treatment of said antigen coated erythrocytes with a cross-linking agent; and
   (ii) incubating said sample with said stabilized, antigen coated erythrocyte suspension whereby the presence in the fluid sample of antibody to said hemagglutinating virus antigen effects agglutination of the antigen coated erythrocytes.

10. The method as defined in claim 9 wherein said treating is carried out at room temperature for a period of time ranging from 30 minutes to 4 hours and wherein said cross-linking agent ranges in concentration from 0.02 to 0.2% by weight per volume of antigen coated erythrocyte suspension containing 0.1 to 0.4% by volume of antigen coated erythrocytes.

11. A method according to claim 9 wherein said antibody is rubella antibody and said antigen is rubella hemagglutinating antigen.

12. A method according to claim 11 wherein said cross-linking agent is glutaraldehyde.

13. A method according to claim 12 wherein said blocking agent is tris-(hydroxymethyl)aminomethane.

14. A method of producing a stabilized, antigen coated erythrocyte preparation, which method comprises:
   (a) providing a suspension of erythrocytes in buffered saline;
   (b) treating said erythrocyte suspension with a specific hemagglutinating virus antigen to obtain erythrocytes having antigen coating the surface thereof;
   (c) subjecting said antigen coated erythrocytes of Step (b) to at least one of the following:
      (1) treatment with an enzyme;
      (2) treatment with heat;
      (3) treatment with an acid; or
      (4) treatment with an alkylating agent;
   (d) treating said antigen coated erythrocytes of Step (c) with a cross-linking agent to obtain stabilized, antigen coated erythrocytes; and
   (e) treating said stabilized, antigen coated erythrocytes with a blocking agent to eliminate unreacted functional groups associated with treatment of said antigen coated erythrocytes with a cross-linking agent.

15. A stabilized, antigen coated erythrocyte preparation obtained by the method of claim 4.

* * * * *